US007850649B2

(12) United States Patent
Crank et al.

(10) Patent No.: US 7,850,649 B2
(45) Date of Patent: Dec. 14, 2010

(54) MECHANICAL VOLUME CONTROL FOR INJECTION DEVICES

(75) Inventors: Justin M. Crank, Maple Grove, MN (US); Sidney F. Hauschild, St. Paul, MN (US)

(73) Assignee: AMS Research Corporation, Minnetonka, MN (US)

( * ) Notice: Subject to any disclaimer, the term of this patent is extended or adjusted under 35 U.S.C. 154(b) by 30 days.

(21) Appl. No.: 11/937,617

(22) Filed: Nov. 9, 2007

(65) Prior Publication Data

US 2009/0124974 A1 May 14, 2009

(51) Int. Cl.
*A61M 1/00* (2006.01)

(52) U.S. Cl. ...................................... 604/121; 604/118

(58) Field of Classification Search .................. 604/118
See application file for complete search history.

(56) References Cited

U.S. PATENT DOCUMENTS

| | | | | |
|---|---|---|---|---|
| 118,206 | A | 8/1871 | Crowell | |
| 2,621,853 | A | 12/1952 | Bollerup | |
| 2,708,600 | A | 5/1955 | Froidevaux | |
| 2,867,375 | A | 1/1959 | Petersen | |
| 3,212,684 | A | 10/1965 | Svensson et al. | |
| 3,248,950 | A * | 5/1966 | Pursell et al. | 73/864.18 |
| 4,701,162 | A | 10/1987 | Rosenberg | |
| 4,705,502 | A | 11/1987 | Patel | |
| 4,792,330 | A | 12/1988 | Lazarus | |
| 4,848,367 | A | 7/1989 | Avant et al. | |
| 4,873,977 | A | 10/1989 | Avant et al. | |
| 4,909,785 | A | 3/1990 | Burton et al. | |
| 4,911,164 | A | 3/1990 | Roth | |
| 4,932,956 | A | 6/1990 | Reddy et al. | |
| 4,941,808 | A | 7/1990 | Qureshi et al. | |
| 5,047,039 | A | 9/1991 | Avant et al. | |
| 5,123,908 | A | 6/1992 | Chen | |
| 5,152,772 | A | 10/1992 | Sewell, Jr. | |

(Continued)

FOREIGN PATENT DOCUMENTS

| | | |
|---|---|---|
| WO | WO 92/04869 | 4/1992 |

(Continued)

OTHER PUBLICATIONS

Igel et al., "Comparison of Techniques for Vesicourethral Anastomosis: Simple Direct Versus Modified Vest Traction Sutures," Urology, vol. XXXI, No. 6, pp. 474-477 (Jun. 1988).

(Continued)

*Primary Examiner*—Nicholas D Lucchesi
*Assistant Examiner*—Jason Flick
(74) *Attorney, Agent, or Firm*—Kimberly K. Baxter; Gregory L. Koeller

(57) ABSTRACT

A needleless fluid delivery system allowing for selective control of amounts of therapeutic fluids that are administered to treatment sites within a patient. The fluid delivery system includes an injector source and an access device. The fluid delivery system generally includes an adjustable volume control system for selectively metering the amount of therapeutic fluid to be delivered to the treatment location. The adjustable volume control system generally includes a mechanical stop system with a plunger member and a stop member, wherein the plunger member and stop member physically interact to restrict a plunger insertion length which simultaneously controls an amount of therapeutic fluid expelled by said plunger.

14 Claims, 6 Drawing Sheets

U.S. PATENT DOCUMENTS

| | | | |
|---|---|---|---|
| 5,306,226 | A | 4/1994 | Salama |
| 5,322,418 | A | 6/1994 | Comer |
| 5,540,701 | A | 7/1996 | Sharkey et al. |
| 5,545,171 | A | 8/1996 | Sharkey et al. |
| 5,630,709 | A | 5/1997 | Bar-Cohen |
| 5,695,504 | A | 12/1997 | Gifford, III et al. |
| 5,707,380 | A | 1/1998 | Hinchliffe et al. |
| 5,833,698 | A | 11/1998 | Hinchliffe et al. |
| 5,931,842 | A | 8/1999 | Goldsteen et al. |
| 5,964,791 | A | 10/1999 | Bolmsjo |
| 6,024,748 | A | 2/2000 | Manzo et al. |
| 6,119,045 | A | 9/2000 | Bolmsjo |
| 6,149,667 | A | 11/2000 | Hovland et al. |
| 6,193,734 | B1 | 2/2001 | Bolduc et al. |
| 6,238,368 | B1 | 5/2001 | Devonec |
| 6,254,570 | B1 | 7/2001 | Rutner et al. |
| 6,299,598 | B1 | 10/2001 | Bander |
| 6,302,905 | B1 | 10/2001 | Goldsteen et al. |
| 6,391,039 | B1 | 5/2002 | Nicholas et al. |
| 6,416,545 | B1 | 7/2002 | Mikus et al. |
| 6,440,146 | B2 | 8/2002 | Nicholas et al. |
| 6,447,533 | B1 | 9/2002 | Adams |
| 6,461,367 | B1 | 10/2002 | Kirsch et al. |
| 6,485,496 | B1 | 11/2002 | Suyker et al. |
| 6,494,908 | B1 | 12/2002 | Huxel et al. |
| 6,520,974 | B2 | 2/2003 | Tanner et al. |
| 6,530,932 | B1 | 3/2003 | Swayze et al. |
| 6,562,024 | B2 | 5/2003 | Alvarez de Toledo et al. |
| 6,565,579 | B2 | 5/2003 | Kirsch et al. |
| 6,599,311 | B1 | 7/2003 | Biggs et al. |
| 6,602,243 | B2 | 8/2003 | Noda |
| 6,695,832 | B2 | 2/2004 | Schon et al. |
| 6,702,825 | B2 | 3/2004 | Frazier et al. |
| 6,719,709 | B2 | 4/2004 | Whalen et al. |
| 6,719,749 | B1 | 4/2004 | Schweikert et al. |
| 6,726,697 | B2 | 4/2004 | Nicholas et al. |
| 6,740,098 | B2 | 5/2004 | Abrams et al. |
| 6,746,456 | B2 | 6/2004 | Xiao |
| 6,746,472 | B2 | 6/2004 | Frazier et al. |
| 6,821,283 | B2 | 11/2004 | Barzell et al. |
| 2001/0049492 | A1 | 12/2001 | Frazier et al. |
| 2002/0002363 | A1 | 1/2002 | Urakawa et al. |
| 2002/0087176 | A1 | 7/2002 | Greenhalgh |
| 2003/0069629 | A1 | 4/2003 | Jadhav et al. |
| 2003/0208183 | A1 | 11/2003 | Whalen et al. |
| 2003/0229364 | A1 | 12/2003 | Seiba |
| 2004/0078047 | A1 | 4/2004 | Nicholas et al. |
| 2004/0087995 | A1 | 5/2004 | Copa et al. |
| 2005/0070938 | A1 | 3/2005 | Copa et al. |
| 2005/0131431 | A1 | 6/2005 | Copa et al. |
| 2005/0251155 | A1 | 11/2005 | Orban, III |
| 2006/0200178 | A1 | 9/2006 | Hamel et al. |
| 2006/0264985 | A1 | 11/2006 | Copa et al. |
| 2006/0276811 | A1 | 12/2006 | Copa et al. |
| 2007/0219584 | A1 | 9/2007 | Copa et al. |

FOREIGN PATENT DOCUMENTS

| | | |
|---|---|---|
| WO | WO 96/07447 | 3/1996 |
| WO | WO 99/16359 | 4/1999 |
| WO | WO 99/21490 | 5/1999 |
| WO | WO 99/21491 | 5/1999 |
| WO | WO 99/58081 | 11/1999 |
| WO | WO 2004/000135 | 12/2003 |
| WO | WO 2004/000136 | 12/2003 |
| WO | WO 2004/000137 | 12/2003 |
| WO | WO 2004/000138 | 12/2003 |
| WO | WO 2004/034913 | 4/2004 |
| WO | 2007/013070 | 2/2007 |

OTHER PUBLICATIONS

Acconcia et al., "Sutureless" Vesicourethral Anastomosis in Radical Retropubic Prostatectomy, The American Journal of Urology Review, vol. 1, No. 2, pp. 93-96 (Mar./Apr. 2003).

Hruby, G.W., "Comparison of a Novel Tissue Apposing Device and Standard Anastomotic Technique for Vesicourethral Anastomses," Journal of Endourology, vol. 20, Supplement 1 VP12-02, p. A69 (abstract) Aug. 2006.

Hruby, G.W., "Comparison of a Novel Tissue Apposing Device and Standard Anastomotic Technique for Vesicourethral Anastomses," Journal of Urology, vol. 175, No. 4, p. 347, Apr. 2006.

* cited by examiner

FIG. 2
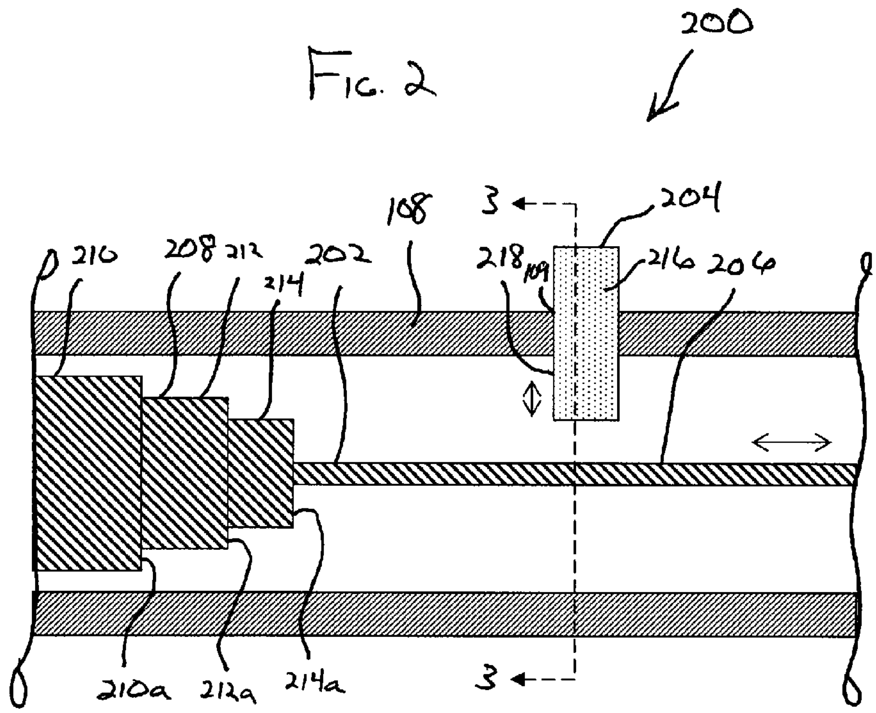
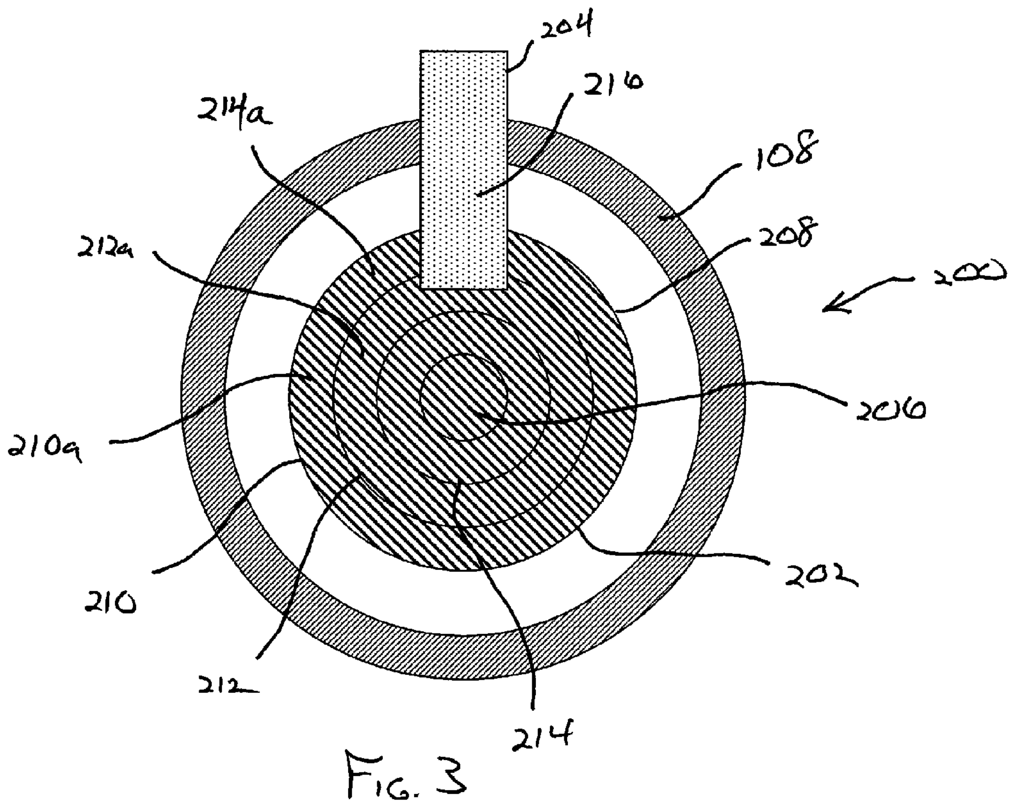
FIG. 3

Fig. 4
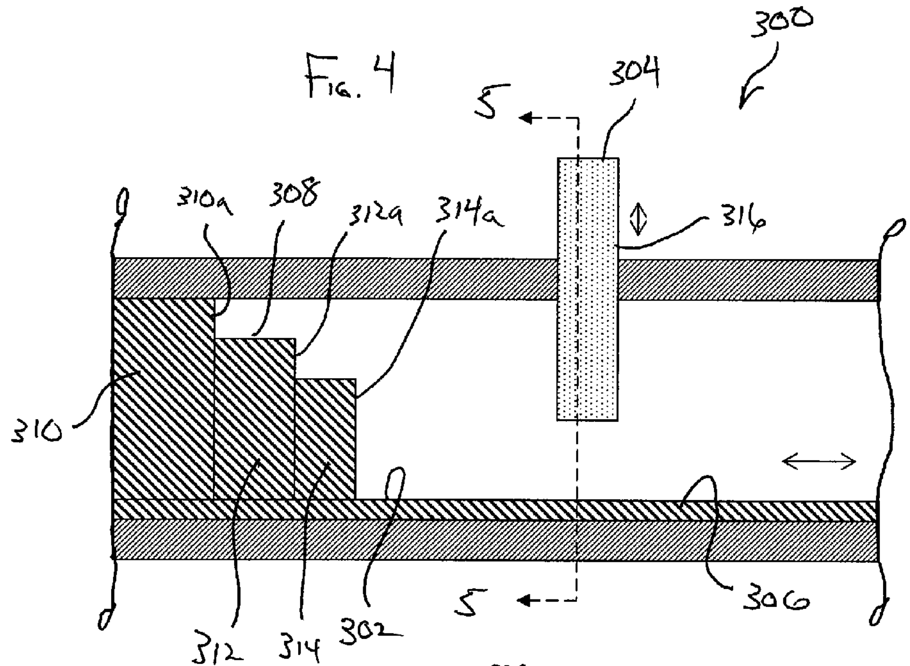
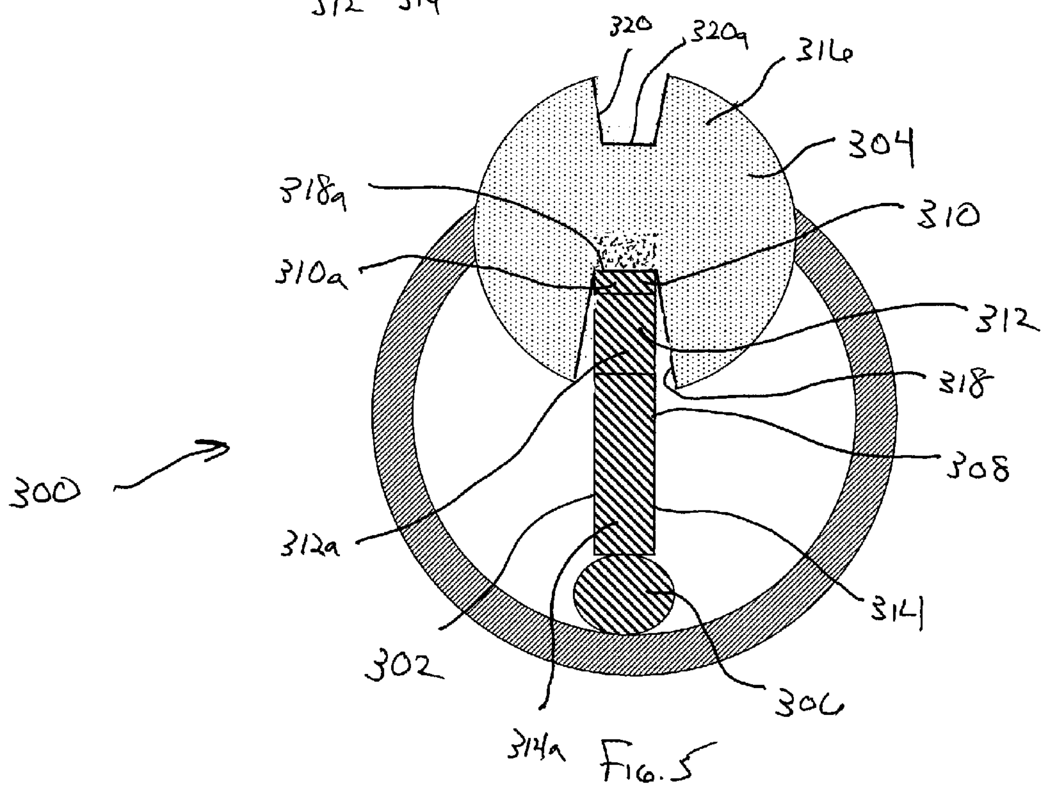
Fig. 5

MECHANICAL VOLUME CONTROL FOR INJECTION DEVICES

PRIORITY CLAIM

The present application claims priority to U.S. Provisional Application Ser. No. 60/856,035, filed Nov. 9, 2006 and entitled, "MECHANICAL VOLUME CONTROL FOR INJECTION DEVICES", which is herein incorporated by reference in its entirety.

FIELD OF THE INVENTION

The present invention relates generally to the delivery of therapeutic fluids. More specifically, the present invention relates to an adjustable mechanical system for accurately delivering measured amounts of a therapeutic fluid to an internal treatment site.

BACKGROUND OF THE INVENTION

A wide variety of medical treatments are at least partially performed through the delivery and introduction of therapeutic compositions to a treatment location. In home or outpatient settings, typical delivery methods can comprise oral delivery, via liquid or solid forms, as well as a variety of inhalant style devices. In clinical or hospital settings, therapeutic fluids can be injected using a needle-based process, or in some minimally invasive procedures the therapeutic fluid can be delivered through a tubular device such as a catheter or endoscope based systems.

When medications are administered at an external location such as, for example, by swallowing the medication, administering a shot or connecting a drip line, the amount of dispensed medication is easily verifiable and controllable simply by measuring and viewing each administration. However, the ability to measure and view each administration of medication is complicated by the inability to actually see delivery with internal applications. In addition, the complexities and time involved in suitably positioning a tubular device at a desired internal location can make the use of individualized applicators impractical such that multiple medication deliveries with a single tubular device are preferred.

Due to the inherent characteristics associated with the delivery of therapeutic compositions to treatment locations within the body, it would be advantageous to have improved procedures and components that provide for accurate and controlled dispensation of therapeutic compositions at internal treatment locations.

SUMMARY OF THE INVENTION

The present invention comprises a fluid delivery system and related methods for adjustably controlling the delivery of therapeutic fluids to treatment sites within a patient. The fluid delivery system can comprise an injector source and an access device. The access device can comprise a minimally invasive, tubular delivery lumen such as a catheter or endoscope. The fluid delivery system generally includes an adjustable volume control system for selectively metering the amount of therapeutic fluid to be delivered to the treatment location. The adjustable volume control system generally includes a mechanical stop system with a plunger member and a stop member, wherein the plunger member and stop member physically interact to restrict a plunger insertion length which simultaneously controls an amount of therapeutic fluid expelled by said plunger. In some embodiments, the stop member can be configured so as to be actuated coaxially with plunger movement while in other embodiments, the stop member may be actuated transversely to the plunger movement. The fluid delivery system can further comprise an imaging system allowing a medical professional to precisely position the access device with respect to a desired treatment location, and which in some embodiments can be used to verify the position of the stop member.

In one aspect of the present disclosure, a fluid delivery system can include an access device having an adjustable volume control for metering and delivering therapeutic fluids to treatment locations within a patient's body. In one presently contemplated embodiment, the access device can comprise a needleless lumen such as a catheter or endoscope for administering the therapeutic fluid in a minimally invasive fashion. The adjustable volume control can comprise a mechanical interface between a stop member and a delivery plunger so as to control a stroke length of the plunger. In some embodiments, the stop member can be actuated in a manner transverse to a travel path of the plunger while in other embodiments, the stop member can be actuated in a coaxial manner with respect to the plunger travel path. In some embodiments, the delivery plunger can be actuated by a delivery shaft that interfaces directly with the stop member to limit a travel length of the delivery plunger.

In another aspect of the present disclosure, a method for selectively metering and administering a volume of a therapeutic fluid with a needleless delivery system can comprise positioning a stop member in a delivery lumen such that the stop member physically interacts with a delivery shaft so as limit a travel length of a delivery plunger. In some embodiments, the stop member can be positioned by biasing a coaxial actuator so as to rotate the stop member to a desired position. Alternatively, the stop member can be positioned by biasing a transverse actuator such that the stop member is inserted to a desired depth within the delivery lumen, wherein the stop member interfaces with the delivery shaft. In yet other embodiments, the delivery shaft can be formed so as to have an engagement profile adapted to selectively interface with the stop member, wherein the engagement profile allows for metering selected volumes of the therapeutic fluid.

In another aspect, the present disclosure is directed to a method for delivering consistently repeatable volumes of a therapeutic fluid to a treatment location within the body with a needle-free delivery system. One representative method for delivering the consistently repeatable volumes of therapeutic fluid can first comprise accessing a treatment location with a minimally invasive access device such as, for example, a catheter or endoscope. Next, a delivery plunger for expelling a volume of pressurized fluid can have its stroke length controlled by limiting a travel length of a delivery shaft coupled to the delivery plunger. The minimally invasive access device can include a stop member that physically and selectively interacts with the delivery shaft. In some embodiments, the delivery shaft can be fabricated so as to have an engagement profile that allows for a variety of travel lengths such that volumes of the pressurized fluid expelled by the delivery plunger can be varied as desired by a medical professional.

The above summary of the various representative embodiments of the invention is not intended to describe each illustrated embodiment or every implementation of the invention. Rather, the embodiments are chosen and described so that others skilled in the art may appreciate and understand the principles and practices of the invention. The figures in the detailed description that follows more particularly exemplify these embodiments.

BRIEF DESCRIPTION OF THE DRAWINGS

The invention may be more completely understood in consideration of the following detailed description of various embodiments of the invention in connection with the accompanying drawings, in which:

FIG. 2 is a cut-away, side view of an embodiment of a delivery volume control apparatus for delivering a therapeutic fluid to a treatment location with a needless fluid delivery system according to the present disclosure;

FIG. 3 is an end view of the delivery volume control apparatus of FIG. 2 taken at line 3-3 of FIG. 2;

FIG. 4 is a cut-way side view of an embodiment of a delivery volume control apparatus for delivering a therapeutic fluid to a treatment location with a needless fluid delivery system according to the present disclosure;

FIG. 5 is an end view of the delivery volume control apparatus of FIG. 4 taken at line 5-5 of FIG. 4;

Figure 1:
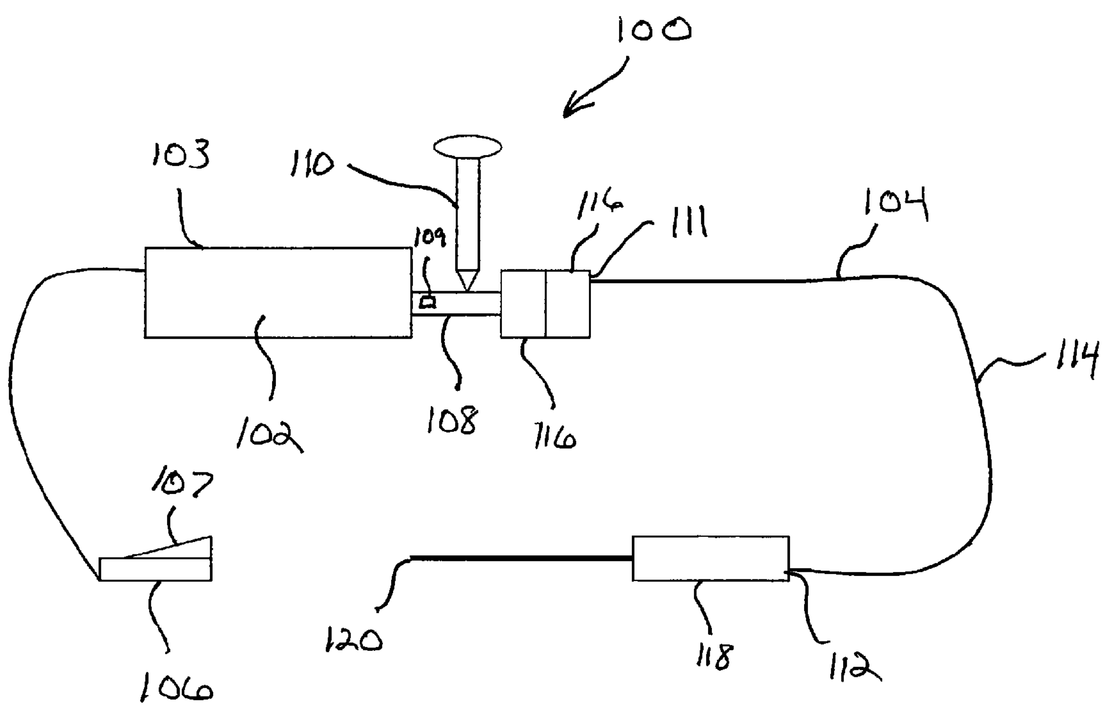
FIG. 1 is a perspective view of an embodiment of a needleless fluid delivery system for delivering a therapeutic fluid to a treatment location according to the present disclosure.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives.

DETAILED DESCRIPTION OF THE DRAWINGS

In the following detailed description of the present invention, numerous specific details are set forth in order to provide a thorough understanding of the present invention. However, it will be obvious to one skilled in the art that the present invention may be practiced without these specific details. In other instances, well-known methods, procedures, and components have not been described in detail so as to not unnecessarily obscure aspects of the present invention.

A needleless fluid delivery system 100 is illustrated generally in FIG. 1. Needleless fluid delivery system 100 can comprise an injector 102 and an applicator lumen 104. Injector 102 can be as simple as manually activated syringe or injector 102 can comprise an automated injector 103 including a user interface 106 and a connector member 108. Connector member can include a surface opening 109 and a therapeutic fluid supply 110. User interface 106 can comprise an input means for selectively delivering a pressurized fluid through the connector member 108. Representative input means can include foot pedal 107, switches, buttons or a touch-screen capable of receiving touch commands as well as displaying system information including a mode of operation as well as operating parameters.

As seen in FIG. 1, applicator lumen 104 generally attaches to the connector member 108. The applicator lumen 104 is generally continuously defined from a supply end 111 to a delivery end 112. Applicator lumen 104 can comprise a variety of configurations including, for example, an endoscope or catheter configuration. In some embodiments, applicator lumen 104 can comprise a flexible tube 114 to allow for easy positioning of the delivery end 112. Supply end 111 is generally configured to attach to the connector member 108 and can include a quick-connect style connector 116. Delivery portion 112 can comprise a variety of configurations depending upon the style of the applicator lumen 104 and a specified treatment location in a patient's body such as, for example, a rectal treatment location, a gastrointestinal treatment location, a nasal treatment location, a bronchial treatment location or an esophageal treatment location. In some embodiments, applicator lumen 104 can include an application specific applicator 118 having a fluid administration port 120.

As illustrated in FIGS. 2 and 3, a delivery volume control apparatus 200 can be incorporated into the needleless fluid delivery system 100. Delivery volume control apparatus 200 generally comprises a plunger shaft assembly 202 and a stop member 204. Delivery volume control apparatus 200 can be fabricated of appropriate material including metals such as stainless steel and nitinol or alternatively, suitable polymeric materials. Plunger shaft assembly 202 can comprise a shaft member 206 and a graduated engagement member 208. Graduated engagement member 208 is generally circumferentially disposed about the shaft member 206 and can include a first engagement portion 210, a second engagement portion 212 and a third engagement portion 214. Each of the engagement portions has a distinct diameter that decreases from the first engagement portion 210 to the second engagement portion 212 and finally to the third engagement portion 214. Each engagement portion includes an engagement surface such as a first engagement surface 210*a* on the first engagement portion 210, a second engagement surface 212*a* on the second engagement portion 212 and a third engagement surface 214*a* on the third engagement portion 214. Shaft member 206 generally extends from the third engagement portion 214 to a plunger (not depicted).

Stop member 204 generally includes a stop body 216 defining a stop surface 218. Stop member 204 can be operably mounted within the connector member 108, or alternatively, within the applicator lumen 104. Stop member 204 is generally configured for retainable placement into surface opening 109 through the use of suitable retention mechanisms including, for example, a friction fit, magnetic coupling, detent means, ratcheted surfaces, spring-loaded retention members and the like.

In use, the stop member 204 is biased into surface opening 109 of connector member 108 such that a desired amount of the stop surface 218 is present within the connector member 108. The amount of stop surface 218 within connector member 108 is selected based upon which of the first engagement surface 210*a*, the second engagement surface 212*a* or the third engagement surface 214*a* is desired to be engaged. By selecting which of the engagement surfaces is engaged, the stroke length of the plunger shaft assembly 202 is limited such that each full stroke delivers the same measured amount of therapeutic fluid through the applicator lumen 104. Through selective placement of the stop member 204, a medical professional can vary the volumetric amount of therapeutic fluid that is ultimately administered at delivery end 112 with each stroke of the plunger shaft assembly 202.

Referring to FIGS. 4 and 5, an alternative embodiment of a delivery volume control apparatus 300 can be incorporated into the needleless fluid delivery system 100. Delivery volume control apparatus 300 generally comprises a plunger shaft assembly 302 and a stop member 304. Delivery volume control apparatus 300 can be fabricated of appropriate material including metals such as stainless steel and nitinol or alternatively, suitable polymeric materials. Plunger shaft assembly 302 generally comprises a shaft member 306 and a step-style engagement member 308. Step-style engagement member 308 can include a first step portion 310, a second step portion 312 and a third step portion 314. Each of the engagement portions has a selected height that decreases from the first step portion 310 to the second step portion 312 and finally to the third step portion 314. Each engagement portion includes an engagement surface such as a first engagement surface 310*a*, a second engagement surface 312*a* and a third engagement surface 314*a*. Shaft member 306 generally extends from the third step portion 314 to a plunger (not depicted).

Stop member 304 generally comprises a circular stop body 316 having a first engagement recess 318 and a second engagement recess 320. Each of the engagement recesses end at a recess surface 318*a*, 320*a*. Stop member 304 can be operably mounted within the connector member 108, or alternatively, within the applicator lumen 104 such that the circular stop body 316 is rotatably positionable. Stop member 304 is generally configured for retainable placement into surface opening 109 through the use of suitable retention mechanisms including, for example, a friction fit, magnetic coupling, detent means, ratcheted surfaces, spring-loaded retention members and the like.

In use, the stop member 304 is rotatably biased such that the desired engagement recess is aligned with the step-style engagement member 308 within the connector member 108. The desired engagement recess is selected based upon which of the step portions is desired to be engaged with the stop member 304. For instance, if a user desires a maximum stroke length, the circular stop body 316 is rotatably positioned such that the first engagement recess 318 is aligned with the step-style engagement member 308. In this configuration, advancement of the plunger shaft assembly 302 results in second step portion 312 and third step portion 314 advancing through the first engagement recess 318 and past the stop member 304 until the circular stop body 316 engages the first engagement surface 310*a* on the first step portion 310. In a similar manner, circular stop body 316 can be rotatably positioned such that recess surface 320*a* engages the second engagement surface 312*a* or that circular stop body 316 immediately engages the third engagement surface 314*a*. By selecting which of the engagement surfaces is engaged by the circular stop body 316, the stroke length of the plunger shaft assembly 302 is limited such that each full stroke delivers the same measured amount of therapeutic fluid through the applicator lumen 104.

Figure 6:
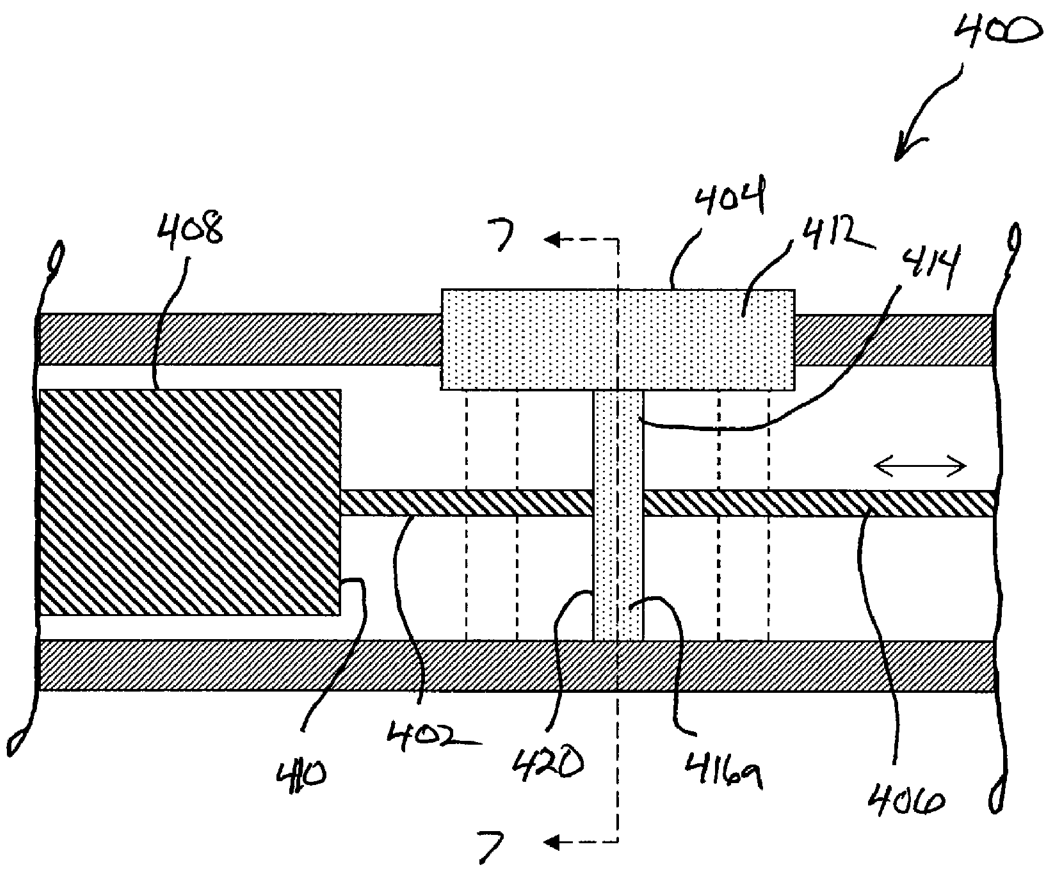
FIG. 6 is a cut-away, side view of an embodiment of a delivery volume control apparatus for delivering a therapeutic fluid to a treatment location with a needless fluid delivery system according to the present disclosure.
Figure 7:
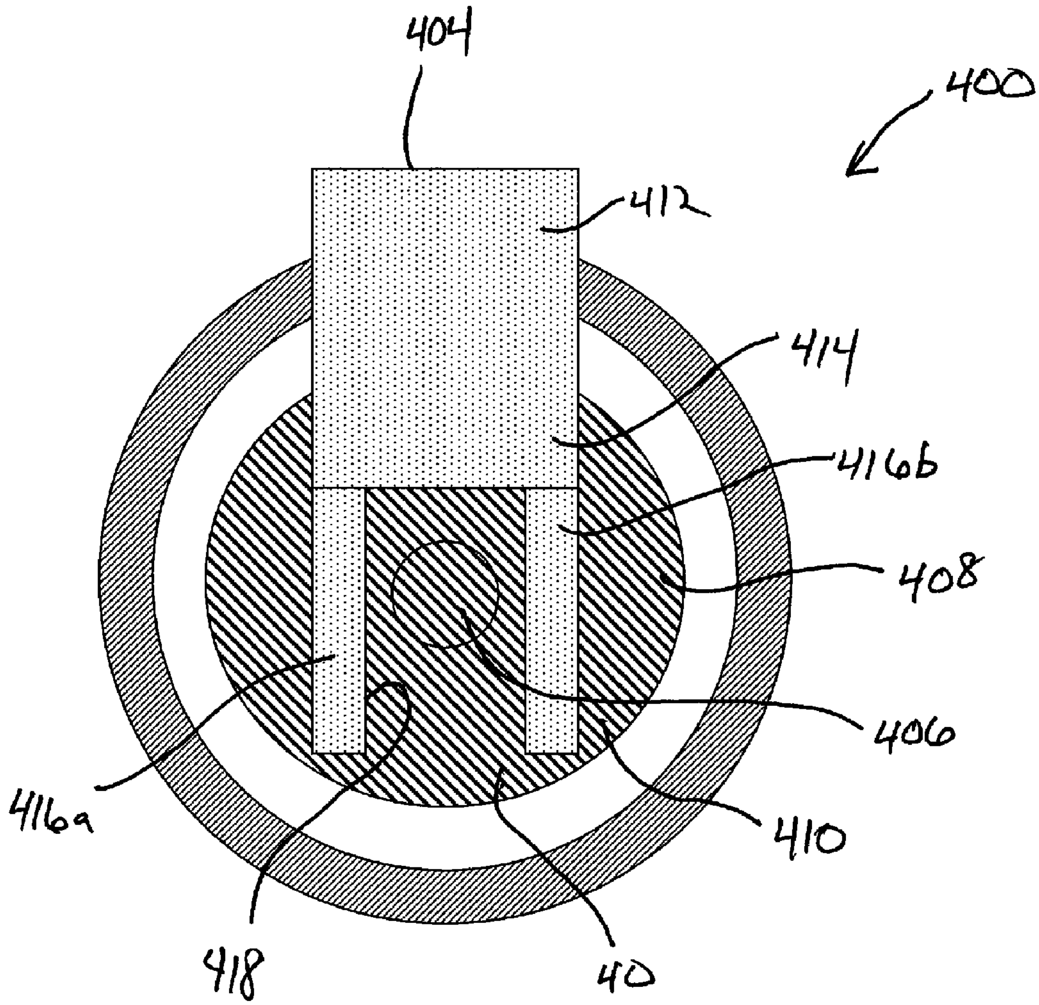
FIG. 7 is an end view of the delivery volume control apparatus of FIG. 6 taken at line 7-7 of FIG. 6.

As illustrated in FIGS. 6 and 7, another alternative embodiment of a delivery volume control apparatus 400 can be incorporated into the needleless fluid delivery system 100. Delivery volume control apparatus 400 generally comprises a plunger shaft assembly 402 and a removable stop member 404. Plunger shaft assembly 402 generally comprises a shaft member 406 and an engagement member 408. Engagement member 408 is generally circumferentially disposed about the shaft member 406 and includes an engagement surface 410. Shaft member 406 generally extends from the engagement surface 410 to a plunger (not depicted).

Stop member 404 generally includes a stop body 412 including a projecting stop member 414. Projecting stop member can include a pair of projecting legs 416*a*, 416*b* which cooperatively define a stop recess 418 with the stop body 412. Stop body 412 further includes a stop surface 420. Removable stop member 404 can be fabricated such that the projecting stop member 414 is located centrally along the stop body 412 or alternatively, at a forward or rear location as shown in phantom in FIG. 7. Stop member 404 can be operably mounted within the connector member 108, or alternatively, within the applicator lumen 104. Stop member 404 is generally configured for retainable placement into surface opening 109 through the use of suitable retention mechanisms including, for example, a friction fit, magnetic coupling, detent means, ratcheted surfaces, spring-loaded retention members and the like.

In use, the stop member 404 is positioned within the connector member 108 such that the projecting stop member 414 is positioned at a desired location with the connector member 108. As the plunger shaft assembly 402 is advanced, the stop recess 418 accommodates the shaft member 406 such that the engagement surface approaches the projecting stop member 414. Further advancement of the plunger shaft assembly 402 is prevented when engagement surface 410 comes into contact with the stop surface 420. By selectively choosing a stop member 404 with the projecting stop member 414 in a desired location, a user controls the length of advancement of the plunger shaft assembly 402 which subsequently controls the amount of a therapeutic fluid administered due to the travel limitations placed on a plunger attached to the shaft member 406.

Figure 8:
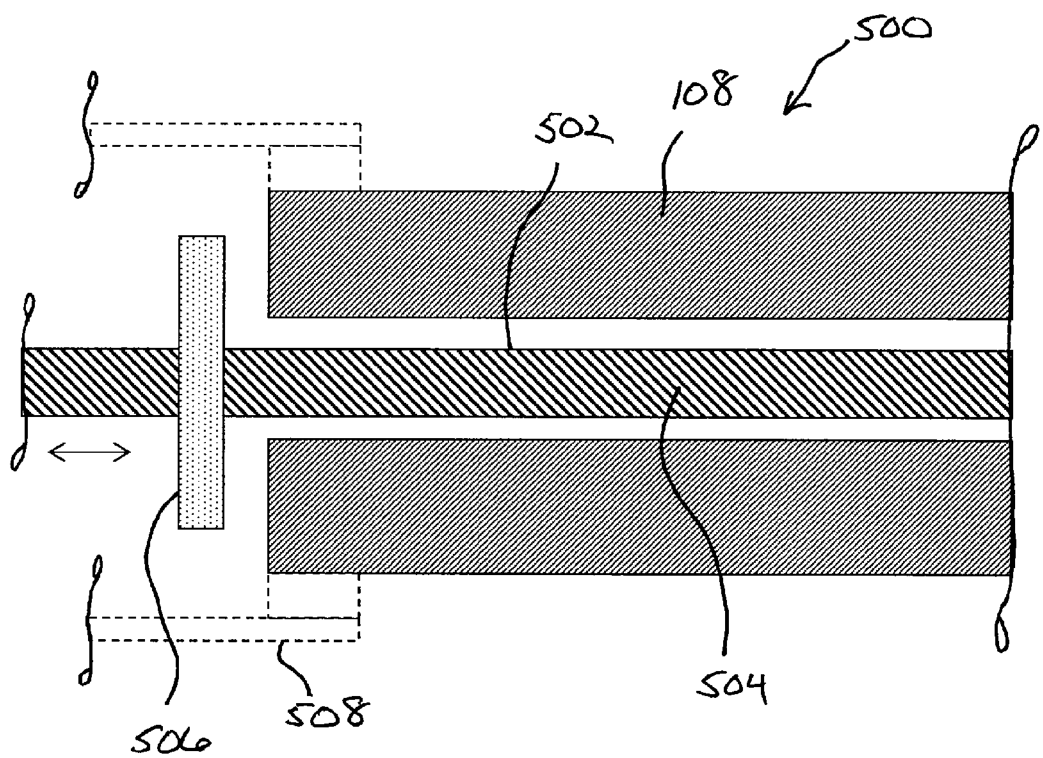
FIG. 8 is a cut-away, side view of an embodiment of a delivery volume control apparatus for delivering a therapeutic fluid to a treatment location with a needless fluid delivery system according to the present disclosure.

As illustrated in FIG. 8, another alternative embodiment of a delivery volume control apparatus 500 can be incorporated into the needleless fluid delivery system 100. Delivery volume control apparatus 500 generally comprises a plunger shaft assembly 502 having a threaded shaft 504 and a threaded stopping nut 506. Threaded shaft member 504 generally extends from the automated injector 102 to a delivery plunger (not depicted). Threaded stopping nut 506 is threadably positioned over the threaded shaft member 504. In some embodiments, threaded shaft member 504 can comprise a visible indicia that indicates various volumetric fluid amounts such that threaded shaft member 504 can be rotatably positioned at a graded measurement area on the visible indicia that corresponds to a desired therapeutic fluid administration amount.

In use, the threaded stopping nut 506 is threadably positioned at the desired location on the threaded shaft member 504. As the plunger shaft assembly 502 is advanced with each stroke, the threaded stopping nut is advanced until it physically encounters connector member 108. Contact between the connector member 108 and threaded stopping nut 506 limits the stroke length of the plunger shaft assembly 502 and ultimately, a plunger that dispenses the therapeutic fluid through the applicator lumen 104. By selectively positioning the threaded stopping nut 506 along the threaded shaft member 504, a medial professional can selectively choose the amount of therapeutic fluid that is ultimately dispensed through the supply end 112 with each stroke of the plunger shaft assembly 502. A shield member 508 can be positioned over connector member 508 and plunger shaft assembly 502 so as to prevent possible pinching as the threaded stopping nut 506 is advanced to the connector member 108.

With respect to the various needle free therapeutic fluid delivery systems described herein, it will be understood that a medical professional preferably utilizes such systems in conjunction with a medical imaging system such as, for example, computer axial tomography (CAT), magnetic resonance imaging (MRI), or in the case of treatment of a prostate gland, the preferred imaging means is transrectal ultrasound (TRUS). Through the use of a medical imaging system, a medical professional can verify that the delivery end 112 is properly inserted and positioned with respect to the desired treatment location.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives.

The invention claimed is:

1. A needleless fluid delivery system comprising:

an applicator lumen;

a connector member; and an injector assembly, the injector assembly including an adjustable volume control apparatus having a plunger shaft assembly and a stop member, the plunger shaft assembly including a shaft member and an engagement portion, the engagement portion including a plurality of engagement surfaces, said engagement surfaces being variably arranged about the shaft member with each engagement surface having differing diameters when measured about the shaft member and, wherein the stop member is positioned such that a desired amount of a stop surface is presented to contact a selected one of the engagement surfaces so as to limit a stroke length of the plunger shaft assembly, and wherein the amount of the stop surface presented is unique for contacting each of the plurality of engagement surfaces.

2. The needleless fluid delivery system of claim 1, wherein the plurality of engagement surfaces define a graduated engagement portion, wherein each engagement surface corresponds to a distinct delivery volume of a therapeutic fluid based on the stroke length of the plunger shaft assembly.

3. The needleless fluid delivery system of claim 2, wherein the plurality of engagement surfaces are circumferentially disposed about the shaft member.

4. The needless fluid delivery system of claim 3, wherein the stop member is operably mounted in a surface opening on the connector member such the stop member can be variably inserted into a connector lumen such that the stop surface selectively engages one of the engagement surfaces on the graduated engagement portion.

5. The needleless fluid delivery system of claim 2, wherein the plurality of engagement surfaces define a step-style engagement member attached to the shaft member.

6. The needleless fluid delivery system of claim 5, wherein the stop member is rotatably mounted in a surface opening on the connector member such that one of a plurality of engagement recesses on the stop member is selectively aligned to contact the desired engagement surface on the step-style engagement member.

7. The needleless fluid delivery system of claim 1, wherein the stop member includes a stop body having a pair of projecting legs defining a stop surface and wherein mounting the stop member within a surface opening on the connector member causes the stop surface to be selectively positioned within the connector member for engaging the engagement portion.

8. A method for adjustably controlling an amount of therapeutic fluid delivered with a needleless fluid delivery system comprising:

providing a needleless fluid delivery system having a minimally invasive access device, a connector member and an injector assembly having a plunger shaft assembly with a plurality of engagement surfaces, said engagement surfaces being variably arranged about the plunger shaft assembly with each engagement surface having differing diameters when measured about the plunger shaft assembly;

accessing a treatment location with the minimally invasive access device;

adjusting a stroke length of the plunger shaft assembly by positioning a stop member such that a desired amount of a stop surface is presented to interact with a selected one of the plurality of engagement surfaces and wherein the amount of the stop surface is unique for engaging each of the plurality of engagement surfaces.

9. The method of claim 8, wherein adjusting the stroke length of the plunger shaft assembly comprises positioning the stop member in a surface opening on the connector member such that the stop surface selectively contacts the selected engagement surface.

10. The method of claim 9, wherein positioning the stop member in the surface opening comprises slidably inserting a desired amount of the stop member into the connector member such that the stop surface selectively contacts the selected engagement surface.

11. The method of claim 9, wherein positioning the stop member in the surface opening comprises rotatably positioning the stop member to align one of a plurality of engagement recesses on the stop member with one of a plurality of engagement surfaces on the engagement member such that a selected recess surface contacts the selected engagement surface.

12. The method of claim 9, wherein positioning the stop member in the surface opening comprises mounting the stop member such that a pair of projecting legs define a stop surface within the connector member and wherein the engagement member contacts the stop surface.

13. The method of claim 8, wherein the delivery shaft comprises a threaded delivery shaft and the stop member comprises a threaded stop member such that adjusting the stroke length of the delivery plunger comprises rotatably positioning the threaded stop member on the threaded delivery shaft such that the threaded stop member selectively contacts the connector member.

14. The method of claim 13, further comprising:

positioning a shield member over the connector member to prevent external exposure to the engagement of the threaded stop member and the connector member.

* * * * *

UNITED STATES PATENT AND TRADEMARK OFFICE

CERTIFICATE OF CORRECTION

PATENT NO. : 7,850,649 B2
APPLICATION NO. : 11/937617
DATED : December 14, 2010
INVENTOR(S) : Justin M. Crank et al.

It is certified that error appears in the above-identified patent and that said Letters Patent is hereby corrected as shown below:

Column 3, line 16, “needless” should be -- needleless --; column 3, line 28, “needless” should be -- needleless --; column 3, line 34, “needless” should be -- needleless --; column 3, line 57, after “as” (second occurrence) insert -- a --.

Column 7, line 39, “needless” should be -- needleless --; column 7, line 41, after “such” insert -- that --.

Signed and Sealed this
Twenty-sixth Day of April, 2011

David J. Kappos
*Director of the United States Patent and Trademark Office*